United States Patent
Luckemeyer et al.

(10) Patent No.: US 10,092,683 B2
(45) Date of Patent: Oct. 9, 2018

(54) FLUID VOLUME MEASUREMENT USING CANISTER RESONANCE FOR REDUCED PRESSURE THERAPY SYSTEMS

(71) Applicant: KCI Licensing, Inc., San Antonio, TX (US)

(72) Inventors: James A. Luckemeyer, San Antonio, TX (US); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 1074 days.

(21) Appl. No.: 14/314,966

(22) Filed: Jun. 25, 2014

(65) Prior Publication Data

US 2015/0025485 A1    Jan. 22, 2015

Related U.S. Application Data

(60) Provisional application No. 61/847,754, filed on Jul. 18, 2013.

(51) Int. Cl.
*A61M 1/00* (2006.01)
*G01F 17/00* (2006.01)
(Continued)

(52) U.S. Cl.
CPC ........ *A61M 1/0088* (2013.01); *A61M 1/0001* (2013.01); *A61M 1/0025* (2014.02);
(Continued)

(58) Field of Classification Search
CPC ........ A61M 1/00; A61M 13/02; A61M 27/00; A61F 13/00; A61B 17/50
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Tatyana Zalukaeva
*Assistant Examiner* — Ilya Treyger

(57) ABSTRACT

A wound fluid collection system includes a canister adapted to collect bodily fluids from a tissue site. The canister includes an acoustic transducer adapted and positioned to insonify a cavity within the canister, the cavity being defined by a wall of the canister and the bodily fluids collected within the canister. A resonant frequency may be calculated based on a resulting received signal from the insonification. The resonant frequency may indicate a volume of the cavity within the canister. The difference between a known volume of the canister and the calculated volume of the cavity provides the volume of bodily fluid collected in the canister.

11 Claims, 3 Drawing Sheets

(51) Int. Cl.
  *G01F 22/00* (2006.01)
  *G01F 23/296* (2006.01)
  *A61M 13/00* (2006.01)
  *A61M 27/00* (2006.01)
  *A61F 13/00* (2006.01)

(52) U.S. Cl.
  CPC ........ *A61M 1/0031* (2013.01); *A61M 1/0092* (2014.02); *G01F 17/00* (2013.01); *G01F 22/00* (2013.01); *G01F 23/2966* (2013.01); *G01F 23/2967* (2013.01); *A61M 2205/21* (2013.01); *A61M 2205/3334* (2013.01); *A61M 2205/3375* (2013.01); *A61M 2205/3379* (2013.01); *A61M 2205/3389* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,251,482 A * | 10/1993 | Bates ...................... G01F 17/00 73/149 |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |
| 2014/0163491 A1 | 6/2014 | Schuessler et al. |
| 2015/0080788 A1 | 3/2015 | Blott et al. |

FOREIGN PATENT DOCUMENTS

| | | | |
|---|---|---|---|
| AU | 755496 | | 2/2002 |
| CA | 2005436 | | 6/1990 |
| CN | WO2013/063848 | * | 1/2006 |
| DE | 26 40 413 A1 | | 3/1978 |
| DE | 43 06 478 A1 | | 9/1994 |
| DE | 295 04 378 U1 | | 10/1995 |
| DE | 10003094 | * | 7/2001 |
| DE | 10003094 A1 | | 7/2001 |
| EP | 0100148 A1 | | 2/1984 |

(56) References Cited

FOREIGN PATENT DOCUMENTS

| | | |
|---|---|---|
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2109934 A | 6/1983 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |
| WO | 94/21311 A2 | 9/1994 |
| WO | 96/05873 | 2/1996 |
| WO | 97/18007 | 5/1997 |
| WO | 99/13793 | 3/1999 |
| WO | 2013/063848 A1 | 5/2013 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "a Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

International Search Report and Written Opinion for PCT/US2014/044182 dated Feb. 26, 2015.

(56) References Cited

OTHER PUBLICATIONS

Partial International Search Report for corresponding PCT/US2014/044182, dated Nov. 6, 2014.

* cited by examiner

FLUID VOLUME MEASUREMENT USING CANISTER RESONANCE FOR REDUCED PRESSURE THERAPY SYSTEMS

RELATED APPLICATION

The present invention claims the benefit, under 35 USC § 119(e), of the filing of U.S. Provisional Patent Application Ser. No. 61/847,754, entitled "FLUID VOLUME MEASUREMENT USING CANISTER RESONANCE FOR REDUCED PRESSURE THERAPY SYSTEMS," filed Jul. 18, 2013, which is incorporated herein by reference for all purposes.

FIELD OF THE INVENTION

The present invention relates generally to tissue treatment systems and in particular to systems and methods for collecting wound fluid.

BACKGROUND OF THE INVENTION

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. The porous pad often is incorporated into a dressing having other components that facilitate treatment. The fluids expressed by the wound are removed through the manifold device by the reduced pressure and transported through a tube connecting the manifold device to a canister. The canister collects the fluids removed from the wound. When the canister is full of fluid removed from the wound, the canister may be emptied and replaced. It may be useful to alert an operator when the canister becomes full.

SUMMARY

In one illustrative embodiment, a reduced pressure treatment system for collecting bodily fluids is provided. The reduced pressure treatment system comprises a canister having a wall and the canister having a volume within. The canister also comprises an inlet adapted to be in fluid communication with a dressing disposed at a tissue site and an outlet adapted to be in fluid communication with a source of reduced pressure. The source of reduced pressure motivates bodily fluids to move from the tissue site into the canister. A cavity within the canister is defined by the wall of the canister and the surface of the bodily fluids within the canister. The reduced pressure treatment system further comprises an acoustic transducer adapted to insonify the cavity of the canister along an axis of insonification at a plurality of frequencies between a first and a second frequency. The acoustic transducer is also adapted to receive an echo output signal resulting from the insonification. The reduced pressure treatment system further comprises a processor in data communication with the acoustic transducer wherein the processor is adapted to determine a resonant frequency wherein the resonant frequency is related to the volume of the cavity.

In an illustrative embodiment, a method of assessing a volume of bodily fluid in a fluid collection device is provided. The fluid collection device comprises a canister having a wall, the wall and the bodily fluid surface defining a cavity within the canister. The method further comprises insonifying the cavity with an acoustic transducer, detecting resulting echo output signals, analyzing the resulting echo output signals, calculating a volume of the cavity based on one or more of the resulting echo output signals, and calculating the volume of the bodily fluid collected in the canister by subtracting the calculated volume of the cavity from a known volume of the canister. The insonifying step may also include insonifying over a range of frequencies and the first calculating step may include determining a resonant frequency of the cavity.

Unless otherwise indicated, as used herein, "or" does not require mutual exclusivity. Other objects, features, and advantages of the illustrative embodiments will become apparent with reference to the drawings and detailed description that follow.

DETAILED DESCRIPTION OF ILLUSTRATIVE EMBODIMENTS

Figure 1:
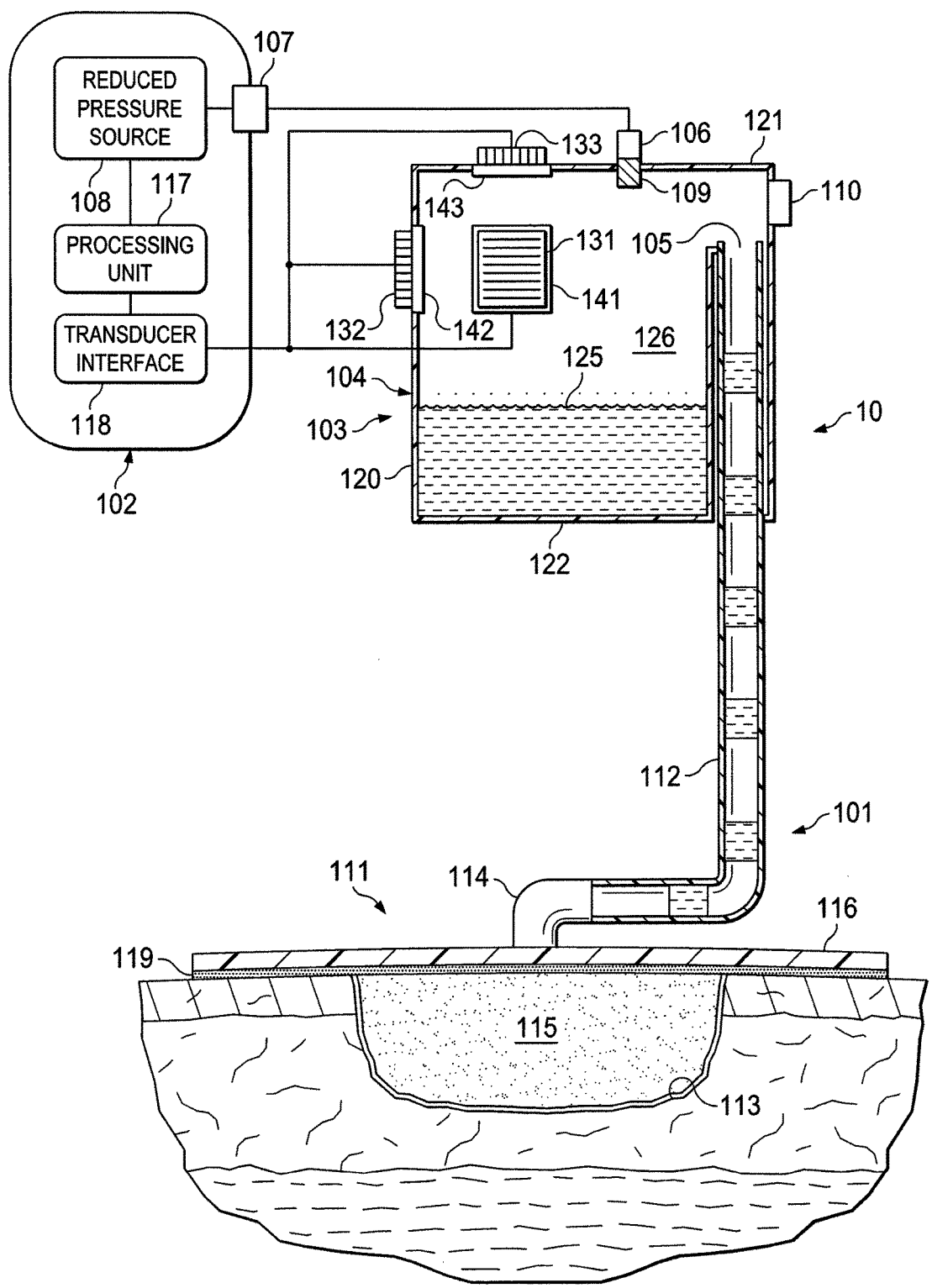
FIG. 1 depicts a sectional view of a reduced pressure treatment system having a fluid collection system, a canister, and a therapy unit according to an illustrative embodiment.

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. Moreover, descriptions of various alternatives using terms such as "or" do not necessarily require mutual exclusivity unless clearly required by the context, and reference to "an" item generally refers to one or more of those items. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The example embodiments may also be described herein in the context of reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Referring to FIG. 1, a reduced pressure treatment system 10 comprises a fluid collection system 101 for applying reduced pressure therapy to a patient, a therapy unit 102 for providing reduced pressure, and a canister 103 fluidly coupled between the fluid collection system 101 and the therapy unit 102 according to one illustrative embodiment. The canister 103 comprises a container 104 having an inlet 105 for providing fluid communication into the container 104 and an outlet 106 for providing fluid communication out from the container 104. The inlet 105 is fluidly coupled to the fluid collection system 101 for providing reduced pressure to the fluid collection system 101 and receiving bodily fluids from the patient. The outlet 106 is adapted to be connected to a reduced pressure port 107 of the therapy unit 102 to provide reduced pressure to the fluid collection system 101 from a reduced pressure source 108 that may be contained within the therapy unit 102. A filter 109 may be disposed proximate or within the outlet 106. The filter 109 may be a hydrophobic filter to help reduce the migration of the bodily fluids to the reduced pressure source 108. The container 104 may be substantially rectangular in shape including sidewalls 120 closed at one end by an upper wall 121 and by a lower wall 122 at the opposite end, all collectively referred to as the "walls" of the container 104. The inlet 105 and the outlet 106 are preferably disposed in the upper wall 121, or in the sidewall 120 proximate the upper wall 121, so that both are positioned at a higher elevation relative to the lower wall 122 during operation.

The container 104 may be constructed of a liquid impervious material such as, for example, a thermoplastic material such as polycarbonate or acrylic or a combination of polycarbonate and acrylic, to contain the exudates or bodily fluids collected from the patient. The container 104 may have a volume that is sufficiently large to accommodate the collection of exudates and bodily fluid from the patient, the level or surface 125 of the bodily fluid rising as the container 104 fills from an empty state to a full state after collecting such fluids. The sidewalls 120 and the upper wall 121 of the container 104 define a void or airspace 126 above the surface 125 of the bodily fluid contained within the container 104. To the extent that the orientation of the canister 103 may change during operation, the position of the surface 125 of the bodily fluid will also change relative to the walls of the container 104 while staying essentially parallel to the horizon.

To determine the extent to which the position of the surface 125 of the bodily fluid may change within the container 104, an orientation detection device 110 may be used to detect the roll and pitch positions of the canister 103. The orientation detection device 110 may be, for example, a motion detection device, an accelerometer or a gyroscope. The canister 103 may also contain sensors that further improve the efficiency of the reduced pressure treatment system 10. In one example, a humidity sensor (not shown) may be disposed within the canister 103 to determine the humidity within the canister 102. In another example, a temperature sensor (not shown) may be disposed within the canister 102 to determine the temperature within the canister 103.

The fluid collection system 101 comprises a wound dressing 111 fluidly coupled to the inlet 105 of the canister 103 via a conduit or tube 112 containing at least one lumen for the transmission of fluids, both gaseous and liquid. The wound dressing 111 is adapted to be positioned proximate the tissue site 113. The wound dressing 111 may comprise a tube connector 114 adapted to be fluidly coupled to the tube 112, and a distribution manifold 115 fluidly coupled to the tube connector 114. The wound dressing 111 may further comprise a drape 116 adapted to cover the distribution manifold 115 for providing a substantially airtight seal over the tissue site 113. The distribution manifold 115 may be a bioabsorbable or bioinert material capable of distributing reduced pressure at various desired levels. The drape 116 may include an adhesive seal 119 that not only maintains the reduced pressure at various levels, but also holds the wound dressing 111 in place over the tissue site 113. In one embodiment, the distribution manifold 115 may be an open cell, reticulated foam comprising, for example, a polyurethane material (for example GranuFoam, Kinetic Concepts, San Antonio, Tex.). The wound dressing 111 delivers reduced pressure to the tissue site 111 to provide therapeutic treatment to the tissue site 111 and to remove exudates and bodily fluids from the tissue site 111. Applied reduced pressure may motivate the bodily fluids from the fluid collection system 101 to the canister 102.

The therapy unit 102 may comprise the reduced pressure source 108, a processing unit 117, and a transducer interface 118. The reduced pressure source 108 may be fluidly coupled to the outlet 106 of the canister 103 via the reduced pressure port 107 for providing reduced pressure to the canister 103. The reduced pressure source 108 may be a reduced pressure or vacuum pump driven by a motor or a piezoelectric device such as, for example, the ultrasonic pump described in U.S. Pat. No. 8,371,829, which is incorporated herein by reference. In another embodiment, the reduced pressure source 108 may be a manually-actuated pump such as a compressible bellows pump. In still another embodiment, the reduced pressure source 108 may be a wall suction port either with or without a separate pressure regulator.

The therapy unit 102 may also contain sensors, alarm indicators, memory devices, databases, software, display units, or user interfaces that further facilitate the application of reduced pressure treatment to the tissue site. In one example, a pressure sensor (not shown) may be disposed at or near the reduced pressure source 108 to determine a source pressure generated by the reduced pressure source 108. The pressure sensor may communicate with the processing unit 117 that monitors and controls the reduced pressure delivered by the reduced pressure source 108. The humidity sensor, the temperature sensor, or the orientation detection device 110 of the canister 103 may also communicate with the processing unit 117.

Still referring to FIG. 1, a first acoustic transducer 131 may be affixed to a first acoustical window 141 of one of the sidewalls 120 of the container 104 and electrically coupled to the transducer interface 118. The first acoustical window 141 comprises an acoustically transparent or transmissive material such as, for example, a rigid material such as polycarbonate or acrylic. It is to be understood that the first acoustical window 141 may be an integral portion of the sidewalls 121 or a separate piece of material disposed in an opening of the sidewalls 121. The first acoustic transducer 131 is oriented to flood the airspace 126 with acoustic waves propagating along an axis substantially normal to the surface of the first acoustic transducer 131, i.e., the first acoustic transducer 131 insonifies the airspace 126 along an axis of insonification which is essentially normal to the surface of the first acoustic transducer 131. The acoustic waves from the first acoustic transducer 131 are reflected by the opposing walls of the container 104 to generate a first echo acoustic wave from the insonification. The first acoustic transducer 131 is adapted to receive the first echo acoustic wave resulting from the insonification and provide a first echo output signal to the transducer interface 118 corresponding to the first echo acoustic wave.

If the canister 103 is designed to be substantially stationary during operation, only one acoustic transducer as described above may be necessary to determine the height of the bodily fluids within the container 104 by insonifying acoustic waves along a single axis. However, if the canister 103 is designed to be part of a portable therapy unit where the container 104 is pitching and rolling around multiple axes such that the surface 125 of the bodily fluids is moving around within the container 104, then a multi-axis insonification system may be desirable.

In another exemplary embodiment, a second acoustic transducer 132 may be affixed to a second acoustical window 142 of one of the sidewalls 120 of the container 104 and electrically coupled to the transducer interface 118. However, the second acoustical window 142 is in one of the sidewalls 120 that is substantially orthogonal to that portion of the sidewalls 120 comprising the first acoustical window 141. The second acoustical window 142 also comprises an acoustically transparent or transmissive material such as, for example, a rigid material such as polycarbonate or acrylic. It is to be understood that the second acoustical window 142 may be an integral portion of the sidewalls 120 or a separate piece of material disposed in an opening of the sidewalls 120. The second acoustic transducer 132 is oriented to insonify the airspace 126 along an axis of insonification which is essentially normal to the surface of the second acoustic transducer 132. The acoustic waves from the second acoustic transducer 132 are reflected by the opposing walls of the container 104 and to generate a second echo acoustic wave from the insonification. The second acoustic transducer 132 is adapted to receive the second echo acoustic wave resulting from the insonification and provide a second echo output signal to the transducer interface 118 corresponding to the second echo acoustic wave. The first acoustic transducer 131 and the second acoustic transducer 132 are oriented to insonify the airspace 126 along separate axes of insonification that are essentially orthogonal to each other. The first and second echo output signals from the first and second acoustic transducers 131, 132, respectively, provide useful information regarding the pitch and roll positions of a portable container 104 that moves around.

In yet another exemplary embodiment, a third acoustic transducer 133 may be affixed to a third acoustical window 143 of the upper wall 121 of the container 104 and electrically coupled to the transducer interface 118. Consequently, the third acoustical window 143 is substantially orthogonal to the sidewalls 120 comprising the first acoustical window 141 and the second acoustical window 142. The third acoustical window 143 also comprises an acoustically transparent or transmissive material such as, for example, a rigid material such as polycarbonate or acrylic. It is to be understood that the third acoustical window 143 may be an integral portion of the upper wall 121 or a separate piece of material disposed in an opening of the upper wall 121. The third acoustic transducer 133 is oriented to insonify the airspace 126 along an axis of insonification which is essentially normal to the surface of the third acoustic transducer 133. The acoustic waves from the third acoustic transducer 133 are reflected generally by the surface 125 of the bodily fluids to generate a third echo acoustic wave from the insonification. The third acoustic transducer 133 is adapted to receive the second echo acoustic wave resulting from the insonification and provide a third echo output signal to the transducer interface 118 corresponding to the third echo acoustic wave. The first acoustic transducer 131, the second acoustic transducer 132, and the third acoustic transducer 133 are each oriented to insonify the airspace 126 along separate axes of insonification that are essentially orthogonal to each other.

The acoustic transducers 131, 132, 133 generate acoustic waves between about 50 Hz and about 20,000 Hz and receive echo acoustic waves in response to reflections within the container 104 for providing echo output signals to the transducer interface 118 as described above. By way of a non-limiting example, the acoustic transducers 131, 132, 133 may be a microphone such as a Brüel & Kjaer model 4180 ½ inch laboratory microphone. The transducer interface 118 is in the electrical communication with the processing unit 117 and configured to provide a control signal alternately to the acoustic transducers 131, 132, 133 wherein the control signal sequentially activates the acoustic transducers 131, 132, 133 to generate acoustic waves at a specific frequency within the range indicated above. The echo output signals are dependent on one or more variables associated with the physical characteristics and dimensions of the container 104, the variable volume ($\Delta V$) of the airspace 126, and the surface 125 of bodily fluids within the container 104. For example, the airspace 126 has a resonant frequency with a damping ratio and a phase shift between the insonification signal and the echo output signal corresponding to the resonant frequency.

The processing unit 117 is configured and programmed to calculate the resonant frequency along with the corresponding damping ratio and the phase shift of the airspace 126 based on the echo output signals provided by the acoustic transducers 131, 132, 133 to the transducer interface 118. This calculation may be formulaic or based on empirical data stored in databases (not shown) associated with the processing unit 117 of the therapy unit 102. If the orientation of the container 104 changes during operation causing the surface 125 of the bodily fluid to change its position such that the bodily fluid covers one or more of the acoustic transducers 131, 132 located in the sidewalls 120, the remaining acoustic transducers that are not covered by the bodily fluid may be utilized for determination of the resonant frequency of the airspace 126.

Figure 2:
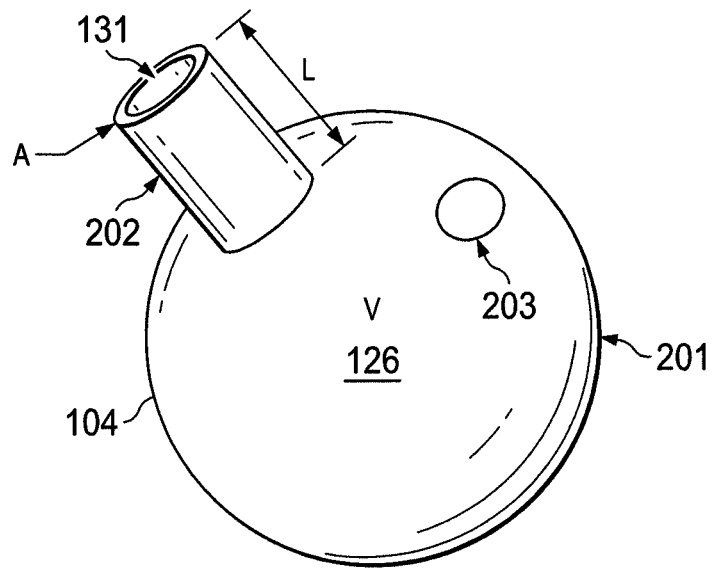
FIG. 2 depicts a perspective view of a container of the canister of FIG. 1 according to an illustrative embodiment.
Figure 4:
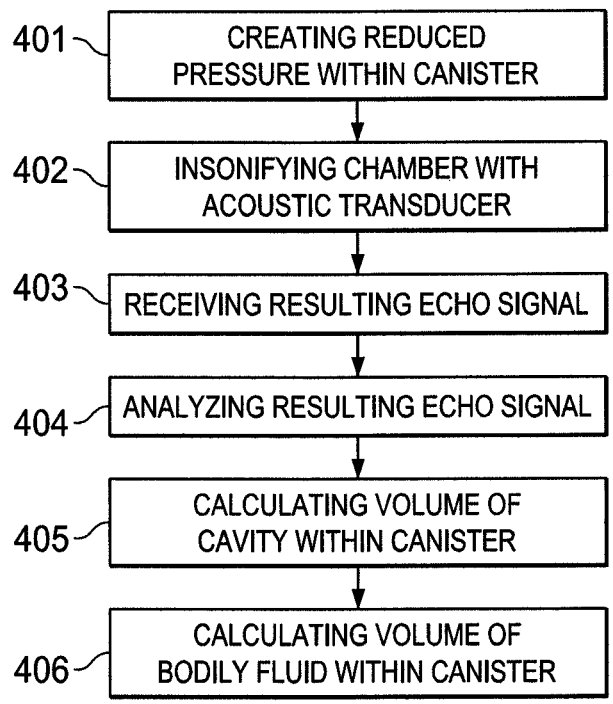
FIG. 4 depicts a method of calculating a volume of a bodily fluid in the reduced pressure treatment system of FIG. 1.

Referring to FIG. 2, by way of an illustrative example, container 104 may comprise a spherical portion 201 in communication with a cylindrical portion 202 that is closed on the end distal to the spherical portion 201, the spherical portion 201 having a volume V and the cylindrical portion 202 having length L and cross-sectional area A. The first acoustic transducer 131 is oriented to insonify the airspace 126 through the closed end of the cylindrical portion 202. The first acoustic transducer 131 is activated at a first frequency f(1) while the power applied by the transducer interface 118 is monitored by the processing unit 117. The first frequency f(1) is then increased to a second frequency f(2) while the processing unit 117 continues to monitor, the power applied by the transducer interface 118. The lowest frequency f between the first frequency and the second frequency that corresponds to a drop in the power required to drive the first acoustic transducer 131 is determined to be a resonant frequency f of the airspace 126 which can be expressed by the following equation (Equation 1):

$$f = \frac{v}{2\pi}\sqrt{\frac{A}{V \cdot L}}$$

where v is the speed of sound. In this example, the volume of the spherical portion of airspace 126 may be calculated from the resonant frequency f by $$V = \left(\frac{v}{2\pi f}\right)^2 \cdot \frac{A}{L}$$

illustrating that the volume V of the spherical portion of the airspace 126 is inversely proportional to the square of the resonant frequency f. The container 104 may also comprise a spherical portion in communication with a cylindrical portion, the spherical portion having an opening defined by edge 203. Because the spherical portion of the container 104 is open to the atmosphere, the volume V of the airspace 126 is essentially infinite such that the airspace 126 would have no resonant frequency according to Equation 1 above.

Figure 3:
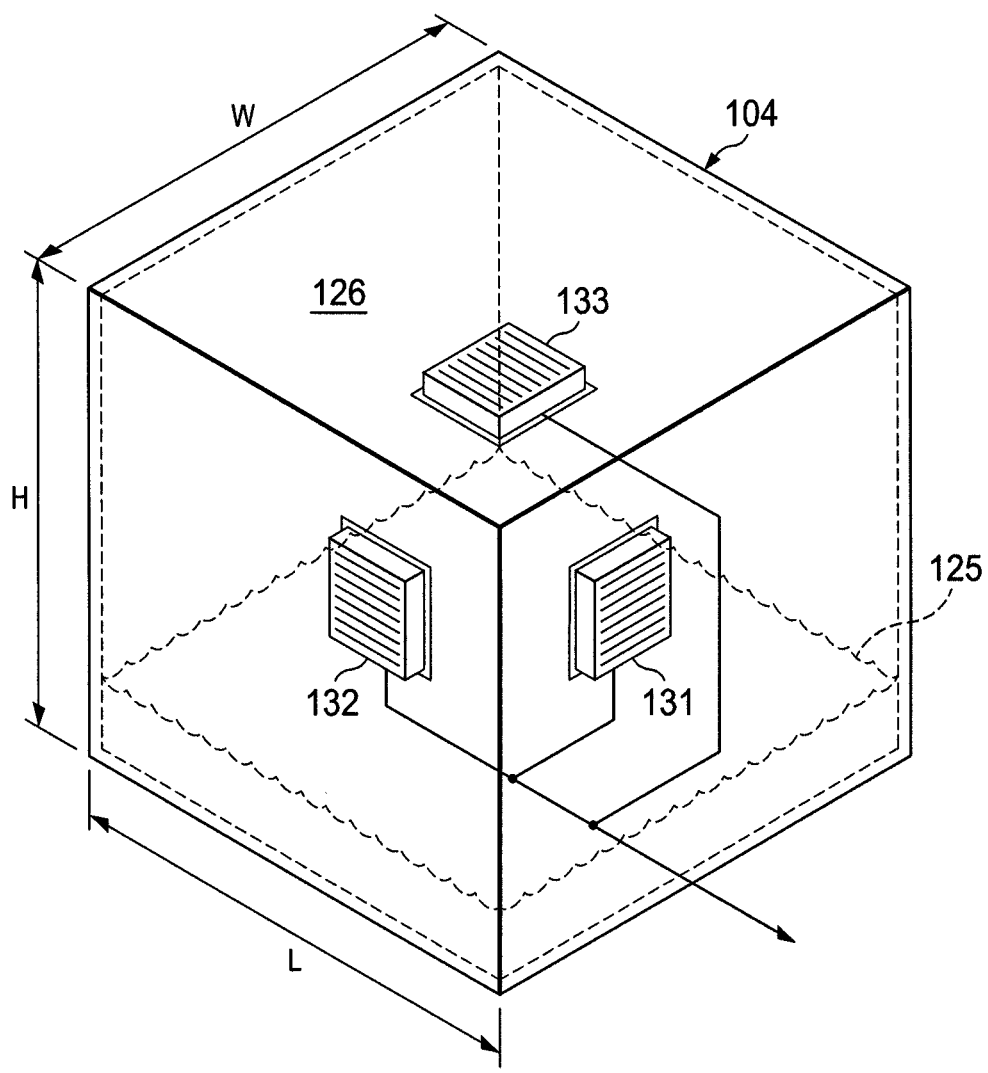
FIG. 3 depicts a perspective view of the container of the canister of FIG. 1 according to an illustrative embodiment.

Referring now to FIG. 3, in another illustrative example, the container 104 may be substantially rectangular in all three projections, having dimensions L, W, and H. The acoustic transducers 131, 132, 133 are oriented to insonify the airspace 126 along the axes of insonification essentially orthogonal to each other, each axis of insonification essentially parallel to an edge of the rectangular container 104. The processing unit 117 and the transducer interface 118 are configured to calculate a volume of the airspace 126 based on a fundamental standing wavelength, w, of each axis. In operation, by way of an illustrative example, the first acoustic transducer 131 is activated at a first frequency while the power applied by the transducer interface 118 is monitored by the processing unit 117. The frequency with which the first acoustic transducer 131 is activated is then increased to a second frequency while the processing unit 117 continues to monitor the power applied by the transducer interface 118. The lowest frequency between the first frequency and the second frequency that corresponds to a drop in the power required to drive the first acoustic transducer 131 is determined to be a fundamental frequency, f, corresponding to a fundamental standing wavelength, λ, along that axis. The fundamental standing wavelength, λ, is the inverse of twice the length dimension, L, along the first axis of insonification, a first half of the wavelength reflecting back a second half of the wavelength. Given that the fundamental frequency, f, is equal to the speed of sound, v, divided by the fundamental standing wavelength, λ, $$f = v/\lambda.$$

the first dimension, L, along the first axis of insonification is given by $$L = v/2f.$$

In operation, this is repeated with the second and third acoustic transducers 132, 133 along the second and third axes of insonification for a second and third dimension, H and W, along the second and third axes. The processing unit 117 then calculates a volume of the airspace 126 as the product of L, H, and W.

In yet another illustrative example, the container 104 may be substantially rectangular in all three projections, having dimensions L, W, and H. The first acoustic transducer 131 is oriented to insonify the container 104. In operation, by way of an illustrative example, the first acoustic transducer 131 is activated at an initial frequency while the power applied by the transducer interface 118 is monitored by the processing unit 117. The frequency with which the first acoustic transducer 131 is activated is increased to a final frequency while the processing unit 117 continues to monitor the power applied by the transducer interface 118. The first lowest frequency between the initial frequency and the final frequency that corresponds to a drop in the power required to drive the first acoustic transducer 131 is determined to be a first modal frequency, f1, corresponding to the first mode wavelength, λ1. The second lowest frequency between the initial frequency and the final frequency that corresponds to a drop in the power required to drive the first acoustic transducer 121a is determined to be a second modal frequency, f2, corresponding to the second mode wavelength, λ2. Subsequent modal frequencies and mode wavelengths are similarly determined.

In yet another illustrative example, the first acoustic transducer 131 is configured to insonify the airspace 126 over a range of frequencies to determine a series of harmonics from which the volume of the airspace 126 is calculated. The processing unit 117 in conjunction with the transducer interface 118 is configured to calculate a volume of the cavity 119 based on a set of harmonics, x, for each of three dimensions according to $$f_x = \frac{v}{2}\sqrt{\left(\frac{i}{L}\right)^2 + \left(\frac{j}{W}\right)^2 + \left(\frac{k}{H}\right)^2}$$

where v is the speed of sound and i, j, and k are the order of the modes along each axis. In this example, the container 104 is substantially rectangular in each projection and is dimensioned such that no edge dimension is more than a multiple of another edge dimension. By way of an illustrative example, the container may have edge dimensions of four, five, and six inches along the three axes since neither five nor six is more than an even multiple of four. Progressively higher harmonics detected from the first acoustic transducer 121a correspond to progressively smaller dimensions of the insonified airspace 126. In this manner, the first three harmonics detected will correspond to the first mode along each axis with the mode of the other two axes being zero. In operation, the lowest harmonic frequency found corresponds to an order of one in a first dimension and zero in a second and a third dimension, removing these quantities from the provided equation. Knowing the frequency of the harmonic, the speed of sound, and the order, the magnitude of that dimension is calculated. The next lowest harmonic frequency found corresponds then to an order of one in the second dimension and zero in the first and third dimensions, eliminating these quantities from the provided equation. The calculation of the magnitude in the second dimension is made in a similar manner. Finally, the third lowest harmonic frequency found corresponds to an order of one in the third dimension and an order of zero in the first and second dimension, removing these quantities from the equation provided. The calculation of the magnitude in the third dimension is made in a similar manner. When each of the first, second, and third dimensions are calculated, the product of these three dimensions is determined, corresponding to the volume of the airspace 126.

In yet another illustrative example, at the time that any one of the first, second, or third acoustic transducers 131, 132, 133 is activated, a check is made by the processing unit 117 to determine if the acoustic transducer is insonifying the airspace 126 or the bodily fluid, in other words, if the acoustic transducer is below the surface 125 of the bodily fluid. By way of example, given that the speed of sound in water is more than four times the speed of sound in air, for the first acoustic transducer 131, the fundamental frequency, f1, would be more than four times higher than would be expected for a canister of known volume. The fundamental frequency, f1, is compared to a threshold and if the processing unit 117 determines that the first acoustic transducer 131 is not insonifying the airspace 126, the processing unit 117 and the transducer interface 118 repeat the process with the second acoustic transducer 132 and, if appropriate, the third acoustic transducer 133. When any of the acoustic transducers 131, 132, 133 is determined to be insonifying the bodily fluid rather than the airspace 126, data from that acoustic transducer is not used in a volume calculation.

A method for assessing a volume of a bodily fluid in a canister is further provided according to an illustrative embodiment. The method includes creating 401 a reduced pressure within the canister to draw the bodily from the tissue site to the canister. The canister includes a wall to contain the bodily fluid and a cavity defined by the wall and the bodily fluid surface and the canister includes a first acoustic transducer oriented to insonify the cavity and to receive a first echo output signal. The canister may include an orientation detection device. The method further includes insonifying 402 the cavity with the first acoustic transducer along a first axis, receiving 403 a resulting first echo output signal, analyzing 404 the resulting first echo output signal, calculating 405 a volume of the cavity based on the resulting first echo output signal, and calculating 406 the volume of the bodily fluid in the canister, the difference in the volume of the canister and the volume of the cavity being the volume of the bodily fluid in the canister.

In one illustrative embodiment, the calculating of the volume of the cavity further comprises assessing a signal from the orientation detection device, accessing a database of echo output signals, orientation detection device signals, and corresponding cavity volumes that have been determined empirically, and matching the resulting echo output signal and orientation detection device signal with the corresponding empirically determined cavity volume. In another illustrative embodiment, the calculating of the volume of the cavity further includes the step of comparing the calculated volume of the cavity to the known volume of the canister and rejecting the calculation of the volume of the cavity as erroneous if the cavity volume is determined to be larger than the canister volume.

In another illustrative embodiment, the method includes insonifying the cavity with the first acoustic transducer, receiving the resulting echo output signal, and comparing a first time difference between initiation of the insonification and reception of the resulting echo output signal, the first time difference being proportional to the length along the axis. The method further includes insonifying the cavity with a second and a third acoustic transducer along a second and a third axis, respectively, and in a similar manner, receiving a second and a third echo output signal, determining a second and a third time difference between the insonification to reception of the second echo output signal and the third echo output signal, the second and third time differences being proportional to the length long the respective axes. The method further includes using one or more of the three time differences to determine the cavity volume. The method may further include determining an orientation of the cavity with an orientation detection device and selecting which one or more of the three time differences to use for the cavity volume calculation based on the orientation of the cavity.

A method for assessing a rate of collection of a bodily fluid in a canister is provided according to another illustrative embodiment. The method includes creating a reduced pressure within the canister to draw the bodily fluid from the tissue site to the canister. The canister includes a wall to contain the bodily fluid and a cavity defined by the wall and the bodily fluid surface and the canister includes an acoustic transducer oriented to insonify the cavity and to receive an echo output signal. The canister may include an orientation detection device. The method further includes insonifying the cavity with the acoustic transducer, receiving a resulting echo output signal, analyzing the resulting echo output signal, calculating a first volume of the cavity based on the resulting echo output signal, repeating the previous steps after a time period calculating a second volume of the cavity, and comparing the first volume to the second volume. In one illustrative embodiment, the calculating of the volume of the cavity further comprises assessing a signal from the orientation detection device, accessing a database of resulting echo output signals, orientation detection device signals, and corresponding cavity volumes that have been determined empirically. The method further includes providing an alert when the calculated rate of collection of the bodily fluid exceeds a threshold.

A method of assessing a viscosity of a bodily fluid collected in a canister is provided according to another illustrative embodiment. The method includes creating a reduced pressure within the canister to draw the bodily from the tissue site to the canister. The canister includes a wall to contain the bodily fluid and a cavity defined by the wall and the bodily fluid surface. The canister includes an acoustic transducer oriented to insonify the cavity with an insonification signal and to receive an echo output signal. The canister may include an orientation detection device. The method further includes insonifying the cavity with the acoustic transducer by providing power to the acoustic transducer, receiving a resulting echo output signal, analyzing the resulting echo output signal, and calculating the viscosity of the bodily fluid in the canister.

In another illustrative embodiment, the calculating step further includes calculating a rate of decay of the resulting echo output signal. In yet another illustrative embodiment, the insonifying step further includes driving the acoustic transducer at a plurality of frequencies between a first frequency and a second frequency. The calculating step further includes calculating the phase angle between the insonification signal and the resulting echo output signal for each of the plurality of frequencies. In still another illustrative embodiment, the insonifying step further includes monitoring the power level provided to the acoustic transducer by the transducer interface and adjusting the power level to achieve a constant vibration amplitude and the analyzing step further includes analyzing the achieved power level.

As described herein, the canister 102 is primarily used to collect exudate from the tissue site 113. Exudates from a small percentage of patients have unique chemical and physical properties. These properties promote bubble formation and foaming as fluid enters the canister, and the fluid may contain proteins that can adhere to many hydrophobic filter membranes forming a residue. When the residue accumulates on the surface of a hydrophobic filter, it may impair filter performance and airflow. This blockage can occur after collecting only a fraction of the canister's capacity, necessitating premature disposal of the canister and increasing operating costs. Under severe conditions, the filter can become completely occluded, which causes the system to fail to deliver the intended treatment. In the extreme case, the occlusion can lead to complete failure of the filter membrane, defeating the primary requirement of separating the fluid from the air, and permitting contamination of downstream components.

A method of removing a residue of a bodily fluid from a canister is provided according to another illustrative embodiment. The canister includes a wall to contain the bodily fluid and a cavity defined by the wall and the bodily fluid surface. The canister includes an inlet and an outlet, the outlet including a filter. The canister further includes an acoustic transducer oriented to insonify the cavity and to receive an echo output signal. The method includes insonifying the cavity with the acoustic transducer at a plurality of frequencies between a first frequency and a second frequency wherein a surface acoustic wave is established on the wall and on the filter of the canister.

It will be appreciated that the illustrative embodiments described herein may be used with reduced pressure treatment systems of any type, shape, or size and similarly with canisters of any type, shape, or size. It should be apparent from the foregoing that an invention having significant advantages has been provided. While the invention is shown in only a few of its forms, it is not just limited but is susceptible to various changes and modifications without departing from the spirit thereof.

We claim:

1. A reduced pressure treatment system for collecting bodily fluids from a tissue site using reduced pressure, comprising:
    a source of reduced pressure;
    a dressing adapted to be disposed proximate and in fluid communication with the tissue site;
    a canister having walls including sidewalls closed by a lower wall and an upper wall for collecting body fluids from the tissue site, an inlet adapted to be in fluid communication with the dressing, and an outlet disposed in the upper wall over the sidewalls proximate the upper wall and adapted to be in fluid communication with the source of reduced pressure, wherein the bodily fluids have a surface rising as the canister fills from an empty state to a full state while collecting the bodily fluids to define an airspace above the surface within the canister;
    a first acoustic transducer acoustically coupled to one of the sidewalls of the canister, configured to insonify the airspace of the canister at predetermined acoustic frequencies along a first axis of insonification including a first frequency and a second frequency, and adapted to generate a first echo output signal in response to acoustic waves reflected within the airspace by opposing walls; and
    a processor in electrical communication with the first acoustic transducer, and adapted to provide input signals to the first acoustic transducer for insonifying the airspace at the predetermined acoustic frequencies, and then for receiving the first echo output signal from the first acoustic transducer to determine a first harmonic frequency being the lowest frequency between the first frequency and the second frequency corresponding to a drop in power required to drive the first acoustic transducer, wherein the first harmonic frequency corresponds to the volume of the airspace.

2. The reduced pressure system of claim 1, further comprising a second acoustic transducer oriented to insonify the airspace of the canister at the first frequency and the second frequency along a second axis of insonification, and adapted to generate a second echo output signal in response to acoustic waves reflected within the airspace by opposing walls, said second acoustic transducer in electrical communication with said processor adapted to provide input signals to the first acoustic transducer to insonify the airspace and to receive the second echo output signal to determine a second harmonic frequency being the lowest frequency between the first frequency and the second frequency corresponding to a drop in power required to drive the second acoustic transducer, wherein the second harmonic frequency corresponds to the volume of the airspace.

3. The reduced pressure treatment system of claim 2, further comprising a third acoustic transducer oriented to insonify the airspace of the canister at the first frequency and the second frequency along a third axis of insonification, and adapted to generate a third echo output signal in response to acoustic waves reflected within the airspace by opposing walls, said third acoustic transducer in electrical communication with said processor adapted to determine a third harmonic frequency being the lowest frequency between the first frequency and the second frequency corresponding to a drop in Dower required to drive the third acoustic transducer, wherein the third harmonic frequency corresponds to the volume of the airspace.

4. The reduced pressure treatment system of claim 1, where said first frequency is about 50 Hz and said second frequency is about 20 KHz.

5. The reduced pressure treatment system of claim 2, wherein said first axis of insonification and said second axis of insonification are mutually orthogonal.

6. The reduced pressure treatment system of claim 3, wherein said third axis of insonification, said second axis of insonification, and said first axis of insonification are mutually orthogonal.

7. The reduced pressure treatment system of claim 1, wherein the first harmonic frequency is equal to the speed of sound divided by a fundamental standing wavelength equal to twice the length of the first axis of insonification.

8. The reduced pressure treatment system of claim 1, wherein the processor calculates a phase shift of the airspace corresponding to the first harmonic frequency.

9. The reduced pressure treatment system of claim 1, wherein the processor calculates a damping ratio of the airspace corresponding to the first harmonic frequency.

10. A system for collecting bodily fluids from a tissue site using reduced pressure, comprising:

A canister having walls including sidewalls closed by a lower wall and an upper wall defining a cavity for collecting body fluids from the tissue site, the cavity configured to be in fluid communication with the dressing and a source of reduced pressure, wherein the cavity fills from an empty state to a full state while collecting the bodily fluids creating an airspace above the bodily fluids within the cavity;

a first acoustic transducer acoustically coupled to one of the walls and configured to insonify the airspace at a first frequency and a second frequency along a first axis of insonification and to generate a first echo output signal in response to acoustic waves reflected within the airspace by opposing walls; and a processor in electrical communication with the first acoustic transducer, the processor adapted to provide input signals to the first acoustic transducer to insonify the airspace and to receive the first echo output signal to determine a first harmonic frequency indicative of the volume of the airspace, the first harmonic frequency being the lowest frequency between the first frequency and the second frequency corresponding to a drop in power required to drive the first acoustic transducer.

11. The system of claim 10, further comprising a second acoustic transducer oriented to insonify the airspace of the canister at the first frequency and the second frequency along a second axis of insonification and to generate a second echo output signal in response to acoustic waves reflected within the airspace by opposing walls, said second acoustic transducer in electrical communication with said processor adapted to provide input signals to the second acoustic transducer to insonify the airspace and to receive the second echo output signal to determine a second harmonic frequency indicative of the volume of the airspace, the second harmonic frequency being the lowest frequency between the first frequency and the second frequency corresponding to a drop in power required to drive the second acoustic transducer.

* * * * *